(12) United States Patent
Shapiro

(10) Patent No.: US 9,075,015 B2
(45) Date of Patent: Jul. 7, 2015

(54) UNIVERSAL TOOL FOR AUTOMATED GEM AND MINERAL IDENTIFICATION AND MEASUREMENT

(76) Inventor: Frederick W. Shapiro, Fairfax, VA (US)

( * ) Notice: Subject to any disclaimer, the term of this patent is extended or adjusted under 35 U.S.C. 154(b) by 9 days.

(21) Appl. No.: 13/488,175

(22) Filed: Jun. 4, 2012

(65) Prior Publication Data
US 2013/0321792 A1 Dec. 5, 2013

(51) Int. Cl.
*G01N 21/00* (2006.01)
*G01N 21/65* (2006.01)

(52) U.S. Cl.
CPC ...................................... *G01N 21/65* (2013.01)

(58) Field of Classification Search
CPC ........... G01J 3/44; G01N 21/00; G01N 21/47; B23K 26/00; B23K 26/24; H04N 7/18
USPC .......... 356/73, 301, 491; 348/61; 219/121.68, 219/121.79
See application file for complete search history.

(56) References Cited

U.S. PATENT DOCUMENTS

| | | | | |
|---|---|---|---|---|
| 5,818,601 A | * | 10/1998 | Scheps | 356/491 |
| 6,995,839 B1 | * | 2/2006 | Shapiro | 356/301 |
| 7,655,882 B2 | * | 2/2010 | Kaplan et al. | 219/121.68 |
| 2008/0035619 A1 | * | 2/2008 | Hamaguchi et al. | 219/121.79 |
| 2010/0225899 A1 | * | 9/2010 | Treado et al. | 356/73 |
| 2011/0292376 A1 | * | 12/2011 | Kukushkin et al. | 356/73 |
| 2012/0007971 A1 | * | 1/2012 | Schnitzer et al. | 348/61 |

* cited by examiner

*Primary Examiner* — Tarifur Chowdhury
*Assistant Examiner* — Jamil Ahmed
(74) *Attorney, Agent, or Firm* — Michael P. Fortkort, Esq.; Michael P Fortkort PC

(57) ABSTRACT

A tool employs Raman spectroscopy, optical imaging, physical measurements, smart software applications, and custom databases for automated on-site gem and mineral identification, measurement, and authenticity verification. Operators with no technical expertise can perform on-site, fast, nondestructive gem and mineral characterization. A custom smart application for data handling and processing enables applicability with a variety of processors. Automated generation of Raman spectral signatures and subsequent correlation to spectral fingerprints of known materials enables gem and mineral identification and verification in field settings. A single tool provides high resolution digital optical imaging and physical measurement capabilities, enables comprehensive sample characterization and reporting that currently requires multiple tools and significant labor. The Tool also provides the capability for sample analysis, requiring an additional level of technical expertise, to be done remotely at another location by the transmission of the data via a communications link. A rechargeable battery pack is included.

19 Claims, 7 Drawing Sheets

Scanner Sample Identification Mode

Gem and Mineral Identifier Overview

Scanner Internal View

Scanner Sample Optical Imaging Mode

Scanner Sample Identification Mode

Blowup of Sample Mounting Fixture

Scanner Probe With Adaptor

Overview of the Sample Identification and Measurement Process

UNIVERSAL TOOL FOR AUTOMATED GEM AND MINERAL IDENTIFICATION AND MEASUREMENT

FIELD OF THE INVENTION

The present invention relates generally to a method and apparatus for conducting automated measurements, identifications and characterizations, and more particularly to a method and apparatus for conducting automated measurements, identifications and characterizations of gems and minerals.

BACKGROUND

Accurate identification, measurement, and characterization of gems and minerals are time consuming, labor intensive and currently involve the use of multiple tools and methods. In addition, some standard tools used in the gemology trade are not sufficient to accurately differentiate between natural, synthetic, counterfeit, treated, or adulterated minerals and gems. More advanced techniques and technologies requiring significant additional resources, expertise, time, and cost are then required.

The present invention is therefore directed to the problem of developing an apparatus that can achieve the goals of comprehensive gem and mineral identification, verification, measurement, characterization, and reporting using one efficient automated tool.

In addition, the present invention is directed to the problem of eliminating multiple tools employed in standard gem and mineral identification and characterization tasks, while significantly reducing labor and resource requirements while concomitantly increasing accuracy and efficiency.

In addition, the present invention is directed to the problem of developing a method for identification of synthetic, counterfeit, or altered samples that can be accurately and consistently accomplished quickly while requiring minimal operator training or expertise.

Moreover, the present invention is directed to the problem of tracing gems or minerals back to their geographical or manufactured origin to aid in combating the sale of precious gems and minerals to fund illegal activities, such as drug trade and insurrections.

In addition, the present invention is directed to the problem of solving the aforementioned problems with a portable and battery powered device suitable for non-office field environments and for applications requiring use at multiple geographical locations.

SUMMARY OF THE INVENTION

The present invention solves these and other problems by providing rapid, accurate, non-destructive, and automated gem and mineral identification, authentication, proof of adulteration, and place of geological origin using optical scanning and Raman spectroscopy.

A secondary application of the present invention is the ability to simultaneously grade and generate physical measurements of samples by providing high resolution optical digital imaging. This is very useful in gem appraisal, geology, insurance, and forensic applications.

A tertiary application of this present invention is the ability to simultaneously provide accurate carat weight determination of samples under evaluation.

An additional application is the automated generation and dissemination of comprehensive sample reporting containing spectral, optical imaging, physical, and sample identification data. This present invention would eliminate the requirement for multiple tools needed to do standard gem and mineral identification and characterization tasks, significantly reducing labor and resource requirements while increasing accuracy and efficiency.

In addition, since this present invention generates a specific spectral fingerprint of the specimen's chemical structure, identification of synthetic, counterfeit, or altered samples can be accurately and consistently accomplished quickly requiring minimal operator training or expertise. In this form, the present invention has the additional potential capability to trace gems or minerals back to their geographical or manufactured origin by identifying accompanying chemical features that are uniquely indigenous to a particular region of the world or source. This capability carries added significance and benefit to the current world approach in combating the sale of precious gems and minerals to fund illegal activities such as drug trade and insurrections.

Additionally, this present invention provides the ability to generate, examine, and save high resolution optical images of gem and mineral samples. High resolution optical images can be used to measure and grade specimens thus eliminating the need for additional optical microscopy and physical measurement tools. Saved images provide optical fingerprints of specimens that can also be used for insurance or forensic applications. Optical imaging can also provide an easy way to record markings and identifying features in gems, minerals, and the materials used in jewelry mountings. An option for an integrated digital scale provides an additional automated capability to simultaneously generate an accurate mineral carat weight.

The portability and battery powered option of this present invention also makes it highly suitable for non-office field environments and for applications requiring use at multiple geographical locations.

The present invention solves these and other problems by providing an automated universal tool that compares a Raman spectral signature of a sample against a custom Raman spectral database of known samples to identify and verify the authenticity of precious gems and minerals. This process is also used to identify counterfeit, synthetic, treated, and adulterated specimens as well as, potentially, the source of the specimen's origin.

According to a first aspect of the present invention, an apparatus for performing on-site, automated, nondestructive, materials analysis on gem and mineral samples using Raman spectroscopy includes a scanner, a processor containing a custom smart application, and a custom spectral database. The gem and mineral identifier tool scanner employs one or more focused coherent light sources (typically lasers) that illuminate and stimulate the chemical bonds within the sample structure via an optical path. The scanner includes one or more highly sensitive cameras (such as charge coupled devices) to collect emitted radiation. Comprehensive unique control databases are generated and store Raman spectral signatures of known gem and mineral samples. The identification tool automatically generates a composite Raman spectral signature from the specimen. A custom smart application loaded on a processor converts the spectral data to a usable form and compares the processed spectral signature to the signatures of known samples in the control database. The use of a custom smart application to do the spectral comparison and all other data processing and handling provides the flexibility of use with a wide range of processor types such as a smart phone, an I-Pad™, or a laptop.

According to another aspect of the present invention, the scanner may include one or more fiber optic probes, as a part of the optical path to transmit radiation to the sample and back to the scanner.

According to another aspect of the present invention, the apparatus processor may interface directly or wirelessly with the scanner and test fixture. All spectral, optical, physical, and reporting data is generated and stored in digital form enabling rapid remote sample transmission and evaluation using the device wireless interface, when additional analysis is required. In addition, the custom libraries used for spectral comparison can automatically be updated from a remote location using the device wireless interface and processor smart application.

According to another aspect of the present invention, the processor smart application will generate a "best match" response within a specified confidence level based on a statistical algorithm and forward the result to the operator. This data is saved by the processor and stored in a unique file generated for the sample being evaluated.

According to yet another aspect of the present invention, the apparatus may include a memory in which the processor can save and tag the spectral signature, thereby enabling the processor to reset for a next sample when many samples need to be processed rapidly.

According to another aspect of the present invention, a mounting fixture that holds the samples includes a stage that is moveable in the x, y, and z directions with high resolution. This mounting stage can be controlled remotely or physically by the operator, for examination of multiple sample locations or depths, without the need to physically reposition the subject in the test fixture.

According to still another aspect of the present invention, the spectra of multiple locations on an inhomogeneous sample may be added together and saved to provide a composite spectral fingerprint representing all relevant mineral contributors.

According to yet another aspect of the present invention, the spectral fingerprint of a composite sample may be subtracted from the spectra of known minerals from the database to isolate unique extra features thus providing insight into the geographical origin of the original sample or to isolate specific components of the specimen.

According to another aspect of the present invention, a white light is first focused on the mounted sample through the tool's optical path to ensure correct sample mounting. The location of the white light represents the exact location that the coherent light source will be focused. An image of the sample is provided on a screen at the front of the tool and/or at the processor for visual verification and examination.

According to still another aspect of this invention, a high resolution copy of the visual image can be saved and stored in a database using the smart application. The stored image of the sample can be magnified if desired to be used for grading purposes or to provide a digital optical fingerprint of the gem or mineral and identifying features or markings on materials used in jewelry mounting for insurance or forensic applications. This data is saved by the processor and stored in a unique file generated for the sample being evaluated.

According to another aspect of the present invention, the smart application can use the stored optical image of the sample to generate accurate measurements of the surface of the sample and to calculate total sample volume. Sample volume can be then used to calculate accurate carat weight of samples that are mounted and inaccessible to be weighed separately. A custom searchable carat weight correlation database is contained in the smart application that uses the total sample volume and the gem identification data to calculate accurate sample carat weight. This data is saved by the processor smart application and stored in a unique file generated for the sample being evaluated.

According to still another aspect of this invention, rotating optics and a partially coated optical prism can be employed in the scanner to enable the transmission and collection of both the white light and the coherent light radiation using a single optical path.

According to yet another aspect of the present invention, the apparatus includes a fiber optic probe(s) that can be used with or without the sample mounting fixture, for the examination of a variety of sample sizes, shapes, and configurations.

According to another aspect of this present invention, the sample mounting fixture includes a sealable housing designed to surround the optical probe and the sample thus eliminating unwanted ambient light. The optical probe can also be used with an adaptor designed to eliminate unwanted ambient light when examining samples outside of the sealed mounting fixture. The optical probe can be used without any shielding fixtures when operating in environments free of ambient light.

According to another aspect of this present invention, the sample mounting fixture includes a removable locking jeweler's tweezers to be used for ease and accuracy of specimen mounting. A mounting fixture specimen tray can be used without the tweezers for larger and irregular shaped specimens.

According to another aspect of this present invention, the sample mounting fixture may also include an integrated precision scale. The smart application will be loaded with a searchable custom database of standard gem conversion factors for quick determination of gem carat weight. This data is saved by the processor smart application and stored in a unique file generated for the sample being evaluated.

According to another aspect of the present invention, the smart application can use the stored physical surface measurements to generate sample carat weight when evaluating a specimen that is inaccessible to be weighed directly because it is secured in a mounting such as jewelry or a fixture. The smart application can use the sample physical surface measurements to calculate total volume and then utilize the searchable custom gem conversion database in conjunction with the identified sample type to calculate accurate carat weight. This data is saved by the processor smart application and stored in a unique file generated for the sample being evaluated.

According to still another aspect of the present invention, the apparatus may also include computer readable media having encoded thereon instructions that cause the processor to automate capture, processing, and correlation of a Raman signature of the subject to spectra in the database and determine a best match or matches within a designated confidence level, wherein if no matches are found within the designated confidence level a "No Match Found" response may be generated and forwarded to the operator. This data is saved by the processor smart application and stored in a unique file generated for the sample being evaluated.

According to a further aspect of the present invention, the apparatus may also include computer readable media having encoded thereon spectral-correlation software to enable the apparatus to provide the capability to automatically trace a gem or mineral to its geographical or manufacturer origin using a database of known Raman signatures.

According to another aspect of the present invention, the apparatus may include a battery to power it, thereby making the apparatus portable for use in field environments or at multiple geographical locations.

According to still another aspect of the present invention, the apparatus may transmit or receive optical, spectral, and physical data and reporting wirelessly to another location using one of the processor types such as the smart phone.

According to yet another aspect of the present invention custom spectral, optical, and physical libraries contained in the smart application can be updated remotely using the wireless processor interface or manually using the physical interface.

According to another aspect of the present invention, the scanner may include more than one radiation source.

According to still another aspect of the present invention, the apparatus may include computer readable media having encoded software to filter out erroneous spectral features in a sample signature to improve the accuracy of the results.

According to another aspect of the present invention, a method for analyzing a subject includes scanning the subject with a Raman scanner, detecting an emitted radiation from the subject, determining a spectral signature of the emitted radiation from the subject, and comparing the spectral signature of the emitted radiation from the subject against one or more samples to determine if the spectral signature of the emitted radiation matches one of the one or more samples.

According to another aspect of the present invention, one or more points on the subject surface or depth may be scanned without physically repositioning the subject in the test fixture.

According to another aspect of the present invention, on-site automated gem or mineral identification and measurement, on-site sample authenticity and integrity verification, and tracing of a sample to its origin is made possible.

According to yet another aspect of the present invention, a method for analyzing a subject includes automatically generating a Raman spectra of one or more points on the subject, and comparing the spectral signature of the emitted radiation from the subject against one or more samples to determine if the spectral signature of the emitted radiation matches one of the one or more samples.

According to another aspect of the present invention, the spectral signature may be transmitted over a communications link or wirelessly for analysis and/or incorporation into a custom spectral database.

According to still another aspect of the present invention, a custom smart application is used to do all of the spectral processing and comparison providing the flexibility of using a wide range of processor types such as a smart phone, an I-Pad®, or a laptop.

According to yet another aspect of the present invention, a smart application is used to collect and analyze optical data providing sample characterization, measurement, and high resolution digital imaging.

According to another aspect of the present invention, a smart application is used to collect data generated by the integrated apparatus digital scale and automatically determine carat weight appropriate for the specimen type identified using the spectral data and by accessing a custom mineral weight conversion table contained in the smart application.

According to still another aspect of the present invention, a smart application is used to collect and analyze all spectral, optical, and physical specimen data and co-locate it in a software file generated and annotated for the specific sample under evaluation.

According to another aspect of the present invention, the smart application is used to generate a specimen report containing all collected data in an appropriate format for ease of review and evaluation. This report may be transmitted or received wirelessly by the processor enabling remote reporting and analysis, if desired.

According to still another aspect of the present invention, all sample data and reporting may be transmitted over a communications link or wirelessly to a processor at another location for analysis or incorporation into a custom database.

According to yet another aspect of the present invention, white light is first focused onto the specimen to identify the exact spot for analysis. A digital optical image is captured, generated, and saved by a high resolution camera within the scanner.

According to another aspect of the present invention, the saved digital optical image can be magnified to provide an optical fingerprint of the sample for insurance or forensic applications.

According to still another aspect of the present invention, the processor smart application can generate exact sample physical measurements and calculate total volume using the saved optical image and input the data into the comprehensive sample report.

According to another aspect of the present invention, one or more focused coherent light sources (typically lasers) are used to illuminate the sample via an optical path.

According to still another aspect of the present invention, the scanner includes one or more highly sensitive cameras (such as charge coupled devices) to collect emitted radiation.

DETAILED DESCRIPTION

Figure 1:
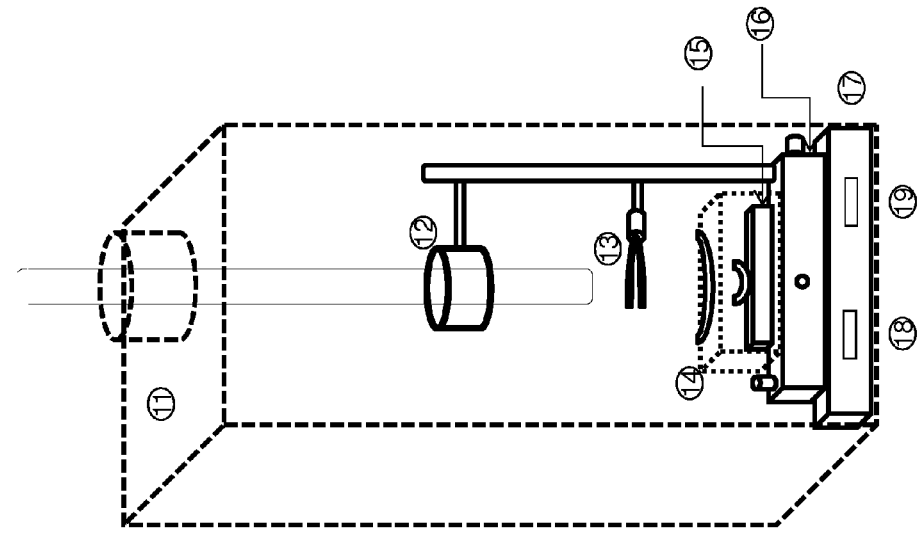
FIG. 1 depicts an exemplary embodiment of a Gem and Mineral Identifier Overview according to one aspect of the present invention.
Figure 1:
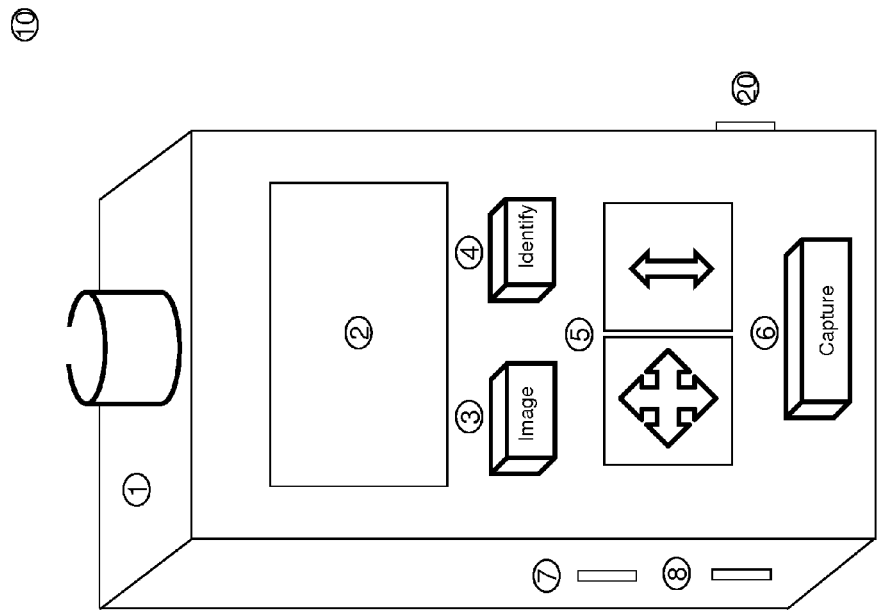
Figure 1:
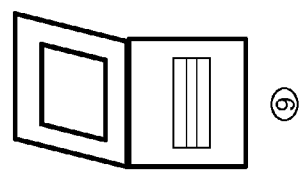

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

This embodiment of the present invention addresses the combination of multiple standard and non-standard tools and processes into a single universal apparatus resulting in an automated scanner using Raman spectroscopy, optical imaging, a smart application, and custom spectral and physical properties databases to be used for on-site gem and mineral identification, verification, measurement, and characterization. Mechanical, optical and software modifications and enhancements are made to conventional Raman spectrographic technology and to standard gemology tools to permit this capability. A custom software smart application is used for the collection, processing, and handling of data enabling a variety of processor types to be utilized.

The universal gem and mineral identification tool of the present invention enables fast, on-site, nondestructive analysis in an automated manner for gem and mineral samples in a non-laboratory environment. The gem and mineral identification and measurement functions are automated to be user-friendly and requires very little user training or technical expertise to operate. The universal gem and mineral identification tool is capable of being portable and battery powered for use in field environments or for use at multiple geographical locations. The universal gem and mineral identification tool can accommodate both large, small, and irregular sized and shaped samples.

Software modifications and the use of a custom smart application enable conventional laboratory Raman spectrographic technology to be converted to an accurate, repeatable, efficient, on-site automated materials analysis capability. The modified Raman spectroscopic technology is employed in conjunction with optical imaging, sample weight determination, a smart software application(s), custom spectral and physical parameter databases, and a variety of processor choices. The smart software application collects, processes and stores all spectral, optical, and physical data in a file tagged specifically for the specimen being evaluated. The smart application then organizes the processed data into a comprehensive sample report that can be printed out or transmitted to another location wirelessly or via a communications link.

Software enhancements permit automatic selection of a number of unique locations of points to be scanned on each subject type. The smart software application permits the operator to automatically reposition the sample and capture spectral and optical data from each new location of interest. Software enhancements contained in the custom smart application enable the spectra from several locations on a single specimen to be added together to generate a composite spectra. The resulting Raman spectral signature may be automatically compared to control spectra in a custom database of known samples for authenticity verification or material identification.

Software enhancements permit sample spectra to be subtracted from the spectra of a known sample to isolate unique additional identifying features. Isolated spectral features can be used to determine sample authenticity, geographical origin, tampering or adulterating, and for fingerprinting, insurance, and forensics applications. The ability to detect counterfeit, synthetic, or adulterated gems and minerals is very useful for appraisers and insurance companies. The ability to trace samples back to their geological origin is very important in the prosecution and prevention of using gems and minerals to fund illicit activities such as insurrections and drug trade. Isolating unique identifying spectral features from a sample can also provide valuable forensic evidence to be used in the prosecution of criminal cases.

The form of the universal gem and mineral identification tool provides a sample mounting fixture that can be adapted for a variety of sample sizes and shapes and for a variety of test environments. The sample mounting fixture includes a base that can be physically or remotely moved with high precision in the x, y, and z directions to enable ease of sample repositioning.

An optical imaging system, also included in the form of the present invention, enables visual identification of exact sample locations to be evaluated. The optical imaging system also enables the capture and storage of digital image recordings of the sample under evaluation. A custom smart application included in the processor portion of the present invention can use the captured digital optical image data to determine accurate sample surface and volume measurements.

A precision digital scale is included in the form of the present invention to enable accurate sample weight determination. This data is then used by the smart application and a custom gem/mineral carat weight conversion database to calculate precise sample carat weight for appraisal, insurance, and forensic applications.

Fiber optic probes are included as a part of the present invention to provide flexibility in evaluating samples that vary significantly in size and shape. The purpose of including fiber optic probes in the optical path of the present invention is to provide a low loss path for the transmission and reception of radiation between the gem and mineral identification tool source and the sample. Conjugated optics are used to efficiently collect and guide light into and out of the fiber optic probes.

A sealable housing is included as an optional part of the sample mounting fixture to prevent ambient light from interfering with the spectral and optical imaging of the specimen under test. The fiber optic probes are fitted with custom adaptors to be used on samples where the use of the apparatus mounting fixture housing is not desirable. Neither the housing nor the adaptor is required for evaluation of specimens in environments devoid of ambient light.

Optical modifications can be made to suit each particular application. The source laser wavelengths selected can be based on the materials of interest for each individual application. Optics selection is optimized for sample spectra signature strength and scanner design parameters, such as size, weight, and power consumption. The optical path is modified from conventional Raman spectroscopic and optical imaging technologies to accommodate a form and function that is portable, efficient, and cost effective. Rotating and partially coated optics are employed in the present invention to enable the use of white and coherent radiation sources both through a single optical path. The universal gem and mineral identification tool can be adapted to include more than one focused coherent light source if the application includes multiple distinct sample types requiring more than one source wavelength. This can be achieved using the single optical path in the present invention or the implementation of multiple optical paths.

A highly sensitive camera is used to detect emitted radiation based on the source laser wavelengths. A single high resolution camera is included in the present invention but the optical path can be modified to easily accommodate more than one camera type if desirable.

A sample of interest is placed within the apparatus mounting fixture. The fixture is designed to accommodate a variety of sample shapes and sizes. A cover or housing is included to surround the mounting fixture if required to shield the sample, preventing ambient light from interfering with the spectral and optical imaging. The scanner fiber optic probe includes an adaptor designed to fit over samples that do not easily conform to the mounting fixture to eliminate the interference of ambient light. The mounting fixture and fiber optic probes are not required for samples being evaluated in environments devoid of ambient light.

A white light source is generated and focused through the scanner optical path into the fiber optic probe. For embodiments of this present invention that include only one optical path, the initiation of the white light source is accompanied by the rotation of certain optical components, providing the desired scanner optical path. The white light is then projected onto the mounted sample surface and an image is transmitted back through the fiber optic probe and captured by the high resolution camera within the scanner. A visible optical image of the sample is generated and provided on the scanner viewer and can also be viewed on the processor screen. The sample is remotely or manually positioned by the operator to the desired location for evaluation. A digital optical imaged is then captured and stored by the smart application in a file specific for that sample. The smart application uses the digital optical image data to generate accurate physical measurements and to calculate total sample volume. This physical data is stored in the sample specific file. The total sample volume can be used by the smart application with a custom carat weight correlation database to calculate the carat weight of samples that are inaccessible for individual physical weighing such as gems in jewelry mountings.

The coherent light source(s) (typically a laser) is then activated and focused through the scanner optical path into the fiber optic probe. For embodiments of this present invention that include only one optical path, the initiation of the coherent light source is accompanied by the rotation of certain optical components providing the desired scanner optical path. The coherent light is then projected onto the mounted sample surface. Scattered Raman radiation is captured by the fiber optic probe and transmitted back to the scanner high resolution camera. Spectral data is then transmitted from the camera to the processor. A Raman spectrum of the sample is generated by the smart application and is then provided on the scanner viewer. The sample spectra can also be viewed on the processor screen. The smart application then initiates a comparison between the sample spectrum and the spectra in the custom database. The automatic comparison of the sample spectrum, to those in one of the custom databases by the smart application, is used for sample identification. A "best match" list is provided to the operator within a predetermined confidence level for the sample identification. If the match is below the preset confidence threshold, a "No Match Found" result will be generated. A result of the sample identification is generated by the smart application and provided to the operator. The sample spectrum and identification result is stored by the smart application in a file specific for that sample.

A precision scale is included in the sample mounting fixture. Processed samples can be individually weighed. This data is used by the smart application and a custom carat weight correlation database to calculate the accurate carat weight of samples. The smart application saves the carat weight determination in the sample specific file.

The smart application uses the spectral, optical, and physical data to create a comprehensive sample specific report. This report can be printed in hardcopy and/or provided in softcopy form. The embodiment includes the ability to transmit sample data and reporting wirelessly or using other communications paths to a remote location for additional analysis by experts if desired or for use by government agencies such as law enforcement. This embodiment also enables the updating of custom searchable spectral, optical, and physical databases remotely through communications links and wirelessly or locally using manually procedures.

The form of the universal gem and mineral identification tool is modified to exhibit a minimal footprint to fit in a relatively small space and to easily be portable. This form is also designed to eliminate the need for several standard currently used trade tools and significantly reduce labor requirements. The types of setting in which the universal gem and mineral identification tool will be used may require limited space and ease of accessibility such as jeweler's office, gemologist or geologist lab, field operations kit, school classroom, museum, pawn shop, U.S. Customs gate, law enforcement vehicle, or a mineral mine.

FIG. 1 shows overview of an exemplary embodiment of a universal gem and mineral identification tool according to a first aspect of the present invention. The universal gem and mineral identification tool scanner 1 is composed of a white light source, a focused coherent light source, an optical path for light transmission, and a high resolution camera. The scanner includes a screen 2 for viewing sample optical images and spectra. Switches that initiate the white light 3 and coherent light 4 sources are provided on the scanner front face. Sample repositioning in the mounting fixture is controlled by the scanner positioning switches 5. Optical imaging is captured using scanner button 6 when the operator is satisfied with the sample location for evaluation. The scanner communicates with the processor 9 using interface 7 or wirelessly and with the power source using interface 8. A fiber optic probe 10 is used to transmit radiation between the scanner and the test sample. A housing 11 is included to shield the test sample from ambient white light during evaluation. A test fixture holder 12 is included to capture and secure the fiber optic probe in place. The sample being evaluated is captured and then secured using a removable fixture 13 such as locking tweezers. Samples too large or irregular shaped to fit into the removable fixture are captured and secured in an alternate sample evaluation tray 14. The small sample holder 13 is removed when using the large sample tray 14. Conversely, this alternate sample tray 14 is removed from the test fixture when the small sample holder 13 is in use. A precision scale 15 is included to obtain an accurate sample physical weight to be used later for the carat weight calculation. An x, y, z adjustable positioning base 16 is incorporated into the test apparatus to enable sample repositioning without the need to physically remove and remount samples from their evaluation holders. The entire sample test fixture is integrated into a base 17 for stability. The test fixture provides an interface 18 for the precision scale 15 and an interface 19 for the adjustable positioning base 16. The scanner includes an interface 20 to the adjustable positioning base interface 19. FIG. 1 also includes a processor 9, depicted in this embodiment as a standard laptop computer. It is important to note that the custom smart application used in this embodiment to capture, control, handle, and process the sample data enables a variety of processor types to be used such as I-Phones, I-Pads, and laptop computers.

Figure 2:
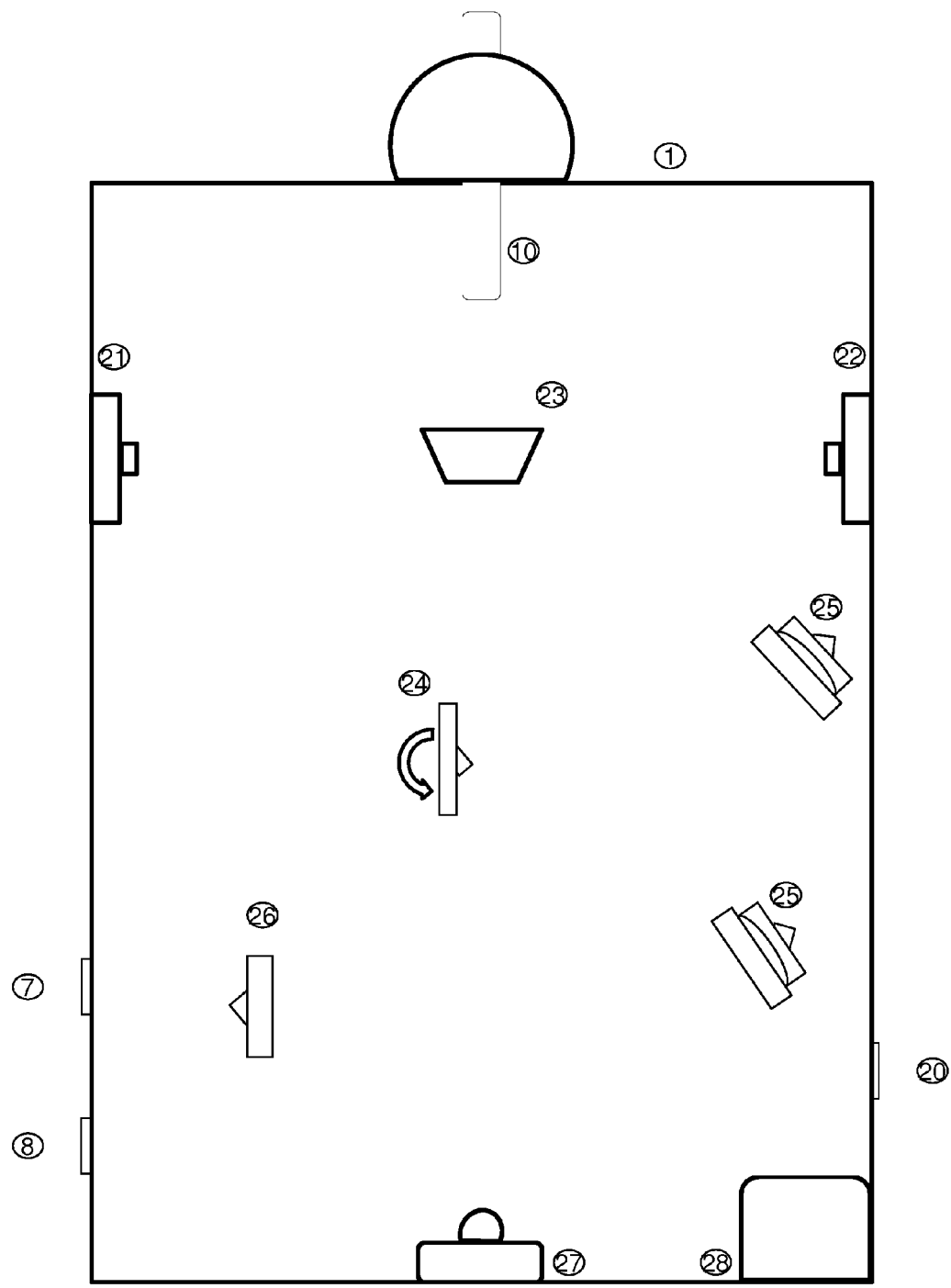
FIG. 2 depicts an internal view of an exemplary embodiment of the Gem and Mineral Scanner Internal View according to another aspect of the present invention.

FIG. 2 depicts an exemplary embodiment of the internal view of the universal gem and mineral identification tool scanner. This internal view of the scanner shows the white light source 21 used for sample positioning and for the generation of digital optical sample imaging. On the opposite side of the scanner is the coherent light source 22 used for generation of sample Raman spectra. The light from each source is projected into a partially coated reflecting prism 23 which then directs the light into the fiber optic probe 10. The prism 23 is coated so that each light source can penetrate the near side uncoated portion of the prism and be reflected towards the fiber optic probe by the coated prism far side surface. The radiation that returns from the sample into the scanner 1 via the fiber optic probe 10 is then focused through an optical path into the high sensitivity camera 27. The scanner optical path consists of the fiber optic probe 10, the partially coated reflecting prism 23, a rotating mirror 24, reflecting minors 25, and an optical gradient 26. The use of a partially coated reflecting prism 23 and a rotating mirror 24 permits the use of one optical path for both the white and coherent light modes thus reducing scanner complexity and physical parameters such as weight and size. A rechargeable battery pack 28 enables the universal gem and mineral identification tool to be used as a portable device.

Figure 3:
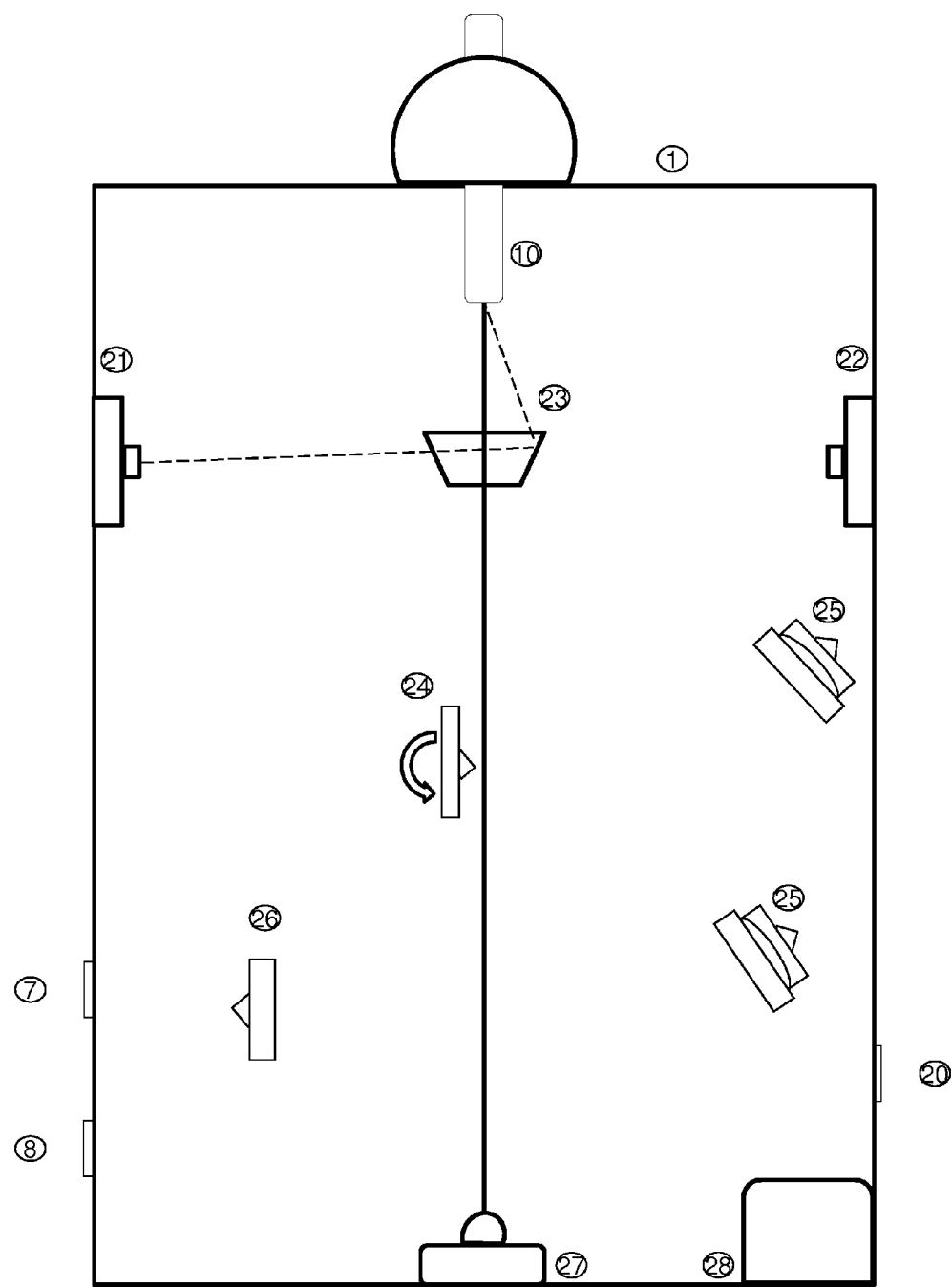
FIG. 3 depicts an internal view of an exemplary embodiment of the Gem and Mineral Scanner Optical Imaging Mode according to yet another aspect of the present invention.

FIG. 3 depicts the scanner sample optical imaging mode operation. The Image switch on the front face of the scanner is selected by the operator. The white light source 21 is then activated and the rotating mirror 24 is positioned to be parallel to the axis between the fiber optic probe 10 and the high sensitivity camera 27. In this position, the rotating mirror 24 is positioned to be outside of the active optical path. White light radiation is transmitted through the uncoated portion of the side of the partially coated reflecting prism 23 closest to the white light source 21 and then reflected off of the coated portion of the far side of the prism into the fiber optic probe 10. White light radiation is then transmitted to the surface of the sample under test by the fiber optic probe 10. Radiation reflected back from the sample is captured by the fiber optic probe 10 and then transmitted back to the scanner 1 from the test fixture. The reflected radiation is then directed through the uncoated top and bottom surfaces of the partially coated reflecting prism 23 and onto the surface of the high resolution camera 27. Data from the high resolution camera 27 is transmitted to the smart application through the scanner to processor interface 7 or wirelessly. An optical digital image is then created and processed by the processor smart application and saved into a file unique to the sample. This optical image data is used by the smart application to generate physical measurements of the sample surface and to calculate total sample volume.

Figure 4:
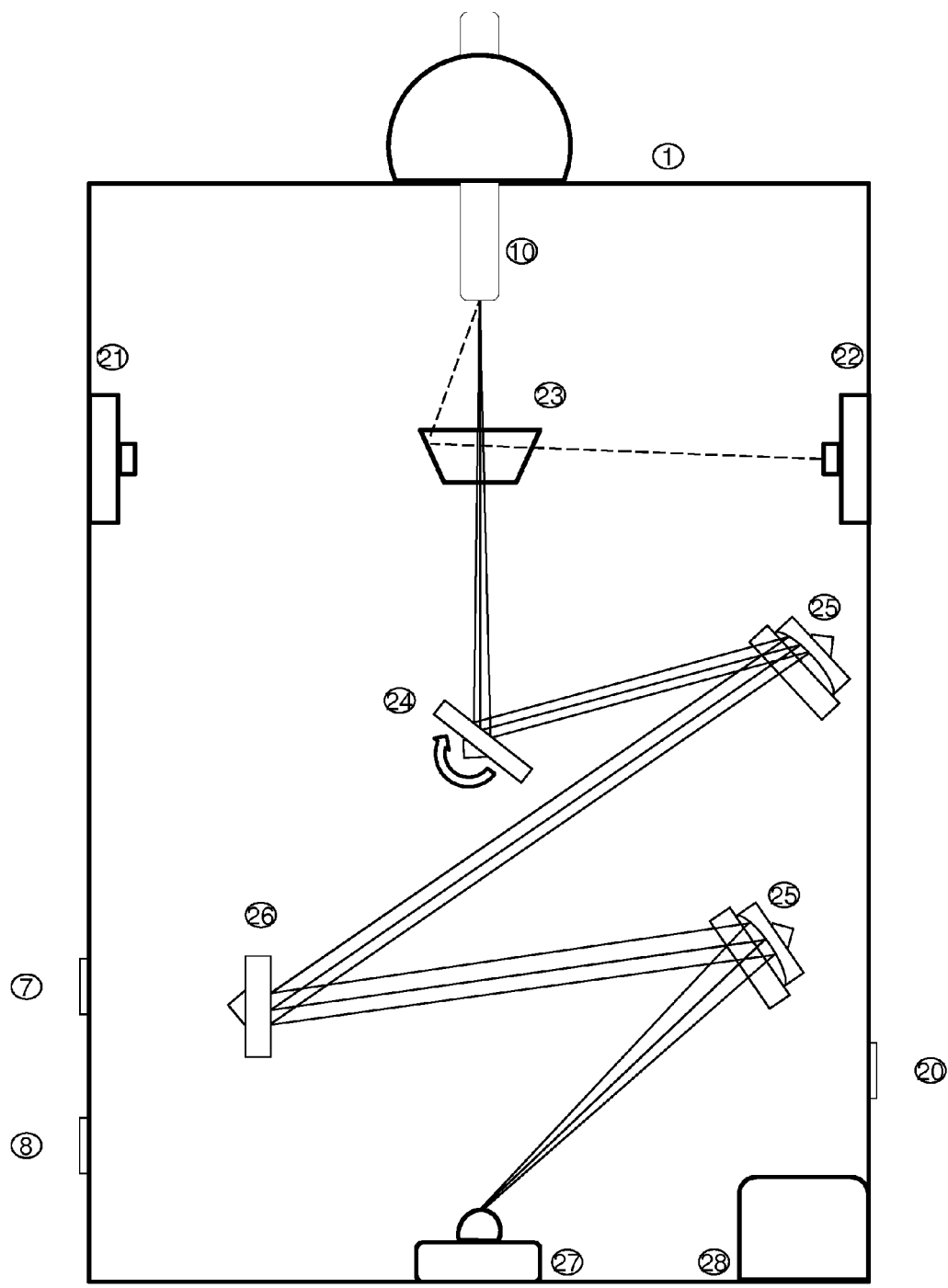
FIG. 4 depicts an internal view of an exemplary embodiment of the Gem and Mineral Scanner Sample Identification Mode according to yet another aspect of the present invention.

FIG. 4 depicts the scanner sample identification mode operation. The Identify switch on the front face of the scanner is selected by the operator. The focused coherent light source 22, which has a wavelength and intensity selected for the particular application, is activated and the rotating mirror 24 is positioned to intersect the axis between the fiber optic probe 10 and the high sensitivity camera 27. In this position, the rotating mirror 24 is positioned at a precise angle to be in line properly with the optical path. Coherent light radiation is transmitted through the uncoated portion of the side of the partially coated reflecting prism 23 closest to the coherent light source 22 and then reflected off of the coated portion of the far side of the prism into the fiber optic probe 10. Coherent light radiation is then transmitted to the surface of the sample under test by the fiber optic probe 10. Radiation reflected back from the sample is captured by the fiber optic probe 10 and then transmitted back to the scanner 1 from the test fixture. The reflected radiation is then directed through the uncoated top and bottom surfaces of the partially coated reflecting prism 23 and onto the surface of the rotating mirror 24. The radiation is then reflected onto mirror 25 and redirected to the optical gradient 26 which separates the shifted radiation into its spectral components. This radiation is then reflected onto the second mirror 25. Radiation from the second reflecting mirror 25 is focused onto the high resolution camera 27. Data from the high resolution camera 27 is transmitted to the smart application through the scanner to processor interface 7 or wirelessly. A Raman spectrum is then created and processed by the processor smart application and then saved into a data file specific for the sample under evaluation. The processor smart application uses specialized correlation software to compare the generated Raman spectrum to a spectral database of known minerals and gems for sample identification. A "best match" within a predetermined confidence level, if any, is generated and transmitted to the operator. The "best match" is also saved in a file unique to the sample under evaluation. The "best match" identification is also used in conjunction with physical weight measurements and the total volume calculation to generate an accurate sample carat weight.

Figure 5:
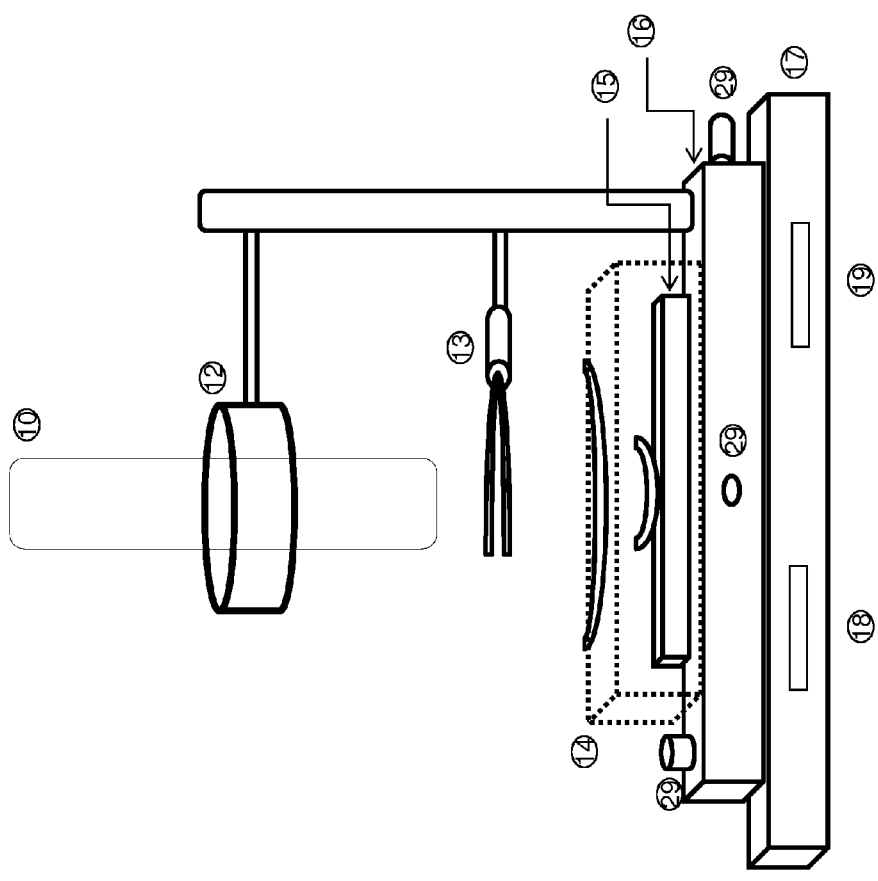
FIG. 5 depicts an exemplary embodiment of a Blowup View of the Gem and Mineral Identifier Sample Mounting Fixture according to another aspect of the present invention.
Figure 6:
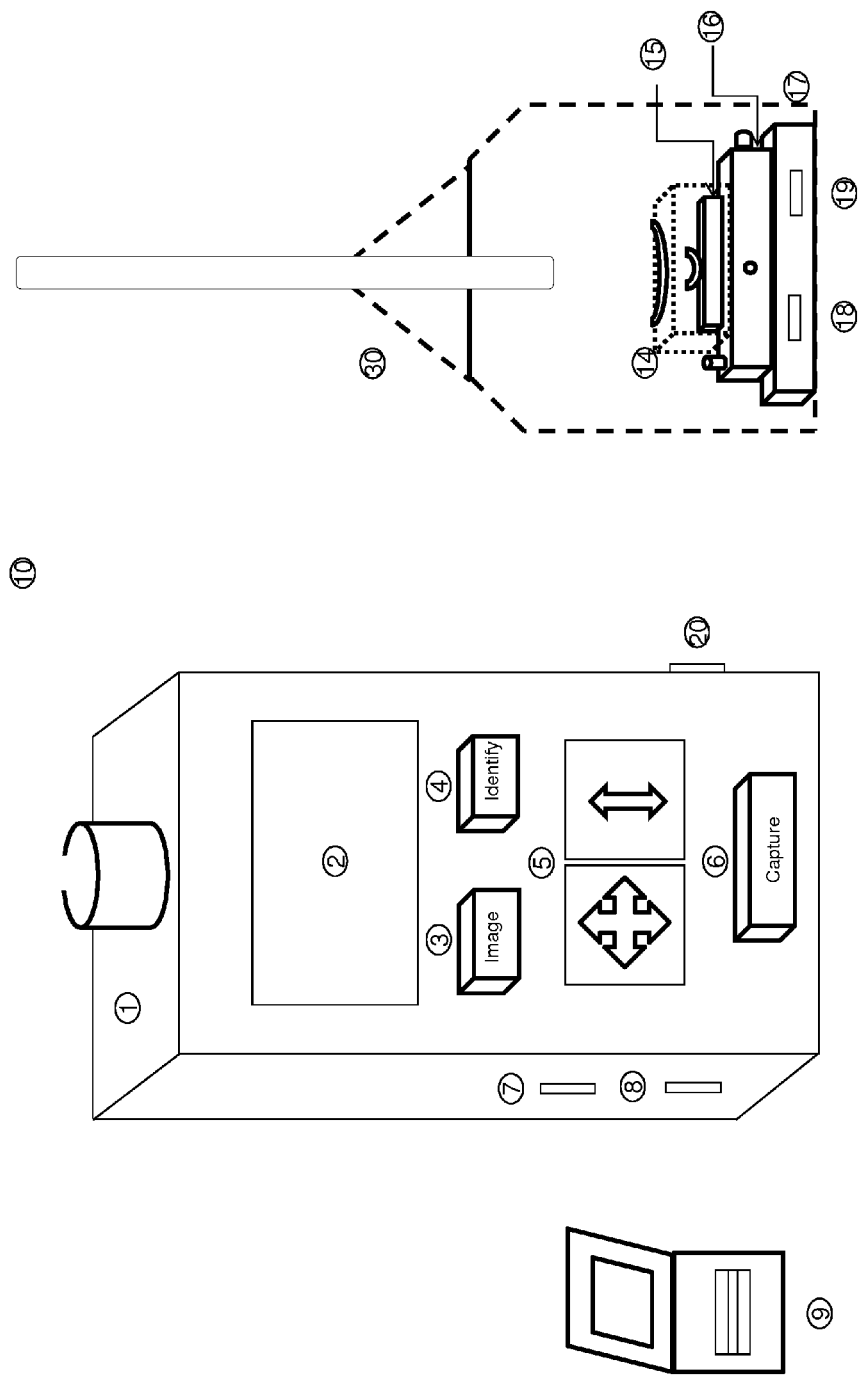
FIG. 6 depicts an exemplary embodiment of a Gem and Mineral Identifier Optical Probe with Adaptor according to another aspect of the present invention.

FIG. 5 represents a blowup view of the sample mounting fixture. As described in FIG. 1 a fiber optic probe 10 is used to transmit radiation between the scanner and the test sample. A test fixture holder 12 is included to capture and secure the fiber optic probe 10 in place. The sample being evaluated is captured and then secured using a removable small sample holder 13 such as locking tweezers. This small sample holder 13 is removed from the test fixture base. A sample is then accessed with the tweezers and locked into place so that the surface to be analyzed is oriented in line with same axis of the fiber optic probe 10. The tweezers are then reattached to the test fixture base. Samples too large or irregular shaped to fit into the removable small sample holder 13 are captured and secured in an alternate sample evaluation tray 14. The small sample holder 13 is removed when using the large sample tray 14. Conversely this alternate large sample tray 14 is removed from the test fixture when the removable small sample holder 13 is in use. A precision scale 15 is included to obtain accurate sample physical weight measurements to be used later for the accurate calculation of carat weight. Sample weight data is transferred to the smart application via an interface 18 located on the test fixture base 17. Sample weight and identification data are used by the smart application to search a correlation database to calculate accurate sample carat weight. Sample weight and carat weight data are stored by the smart application in a file specific for the sample. This data is also automatically included in the comprehensive sample test report. An adjustable x, y, z positioning base 16 is incorporated into the test apparatus to enable sample repositioning without the need to physically remove and remount samples from their evaluation holders. This positioning base 16 can also be repositioned manually using the x, y, and z adjustment knobs 29 if desired. The entire sample test fixture is integrated into a base 17 for stability. The test fixture provides an interface 18 for the precision scale 15 and an interface 19 for the adjustable positioning base 16. The scanner includes an interface 20 to the adjustable positioning base interface 19 to enable remote sample repositioning. FIG. 6 depicts the same embodiment as FIG. 1 with the test fixture housing 11 replaced by the fiber optic probe adaptor 30. The fiber optic probe adaptor 30 is used for samples that don't fit in the test fixture housing 11 or for applications where the test fixture bases 16 and 17 are not required. The adaptor 30 fits tight around the fiber optic probe 10 to prevent ambient light from interfering with the processing of the test sample. The adaptor 30 can come in many shapes, sizes and material types depending on the application. The adaptor 30 may also be rigid or pliable depending on the application.

Figure 7:
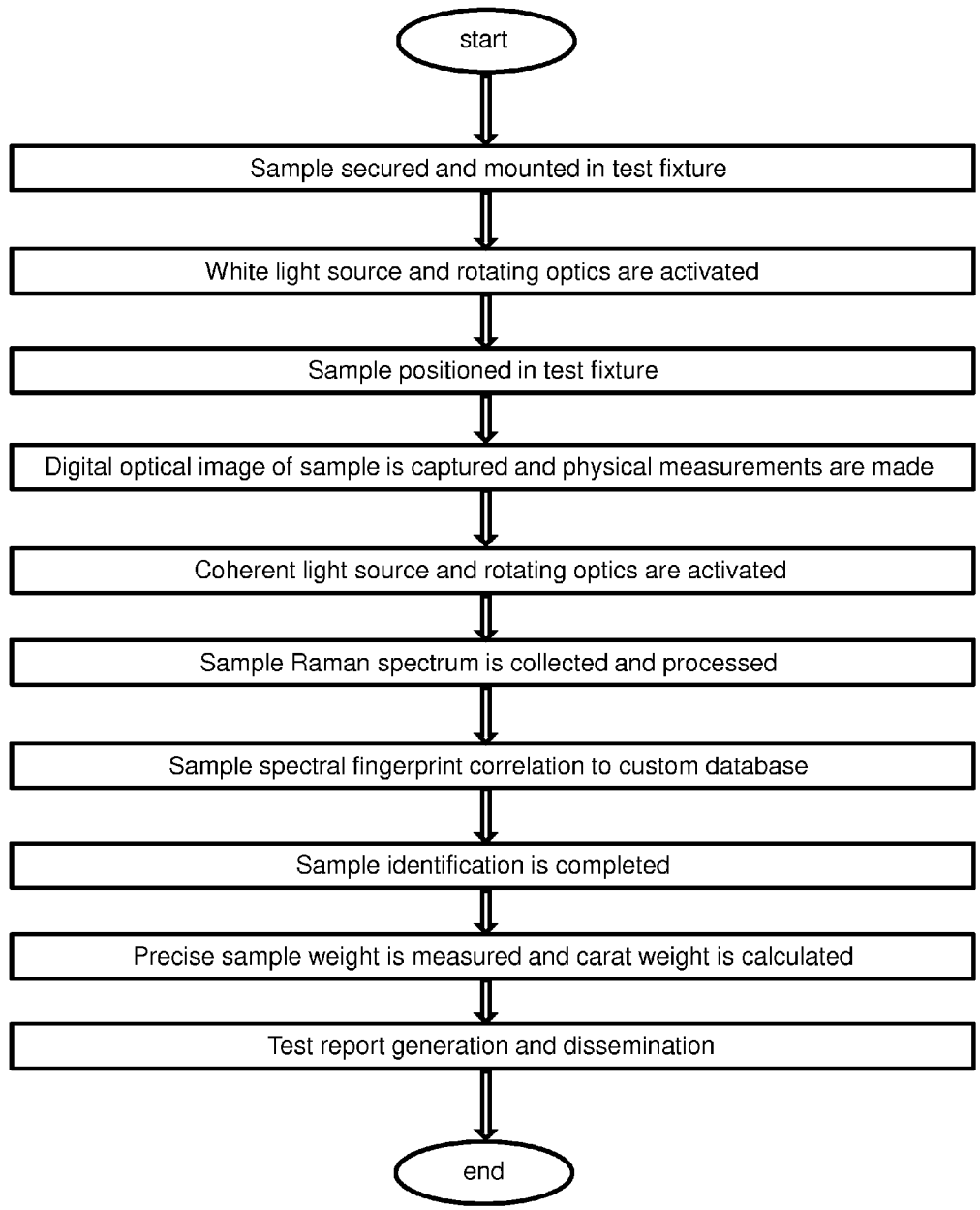
FIG. 7 depicts an exemplary embodiment of an Overview of the Sample Identification and Measurement Process.

FIG. 7 depicts an exemplary embodiment of a method for analyzing a subject.

At step 1, a test sample is mounted in the removable locking tweezers 13 and attached to the test fixture base. If the test sample is too large or irregularly shaped, the locking tweezers are removed from the test fixture and the large sample test fixture tray 14 is used.

At step 2, the Image switch 3 is pressed on the scanner to activate the white light source 21 and the rotating internal optical mirror 24. An optical image will appear on the scanner viewer screen 2 and on the processor screen 9.

At step 3 the sample is repositioned if necessary by the operator using the fixture positioning buttons 5 on the scanner surface or manually using the x, y, and z positioning knobs 29 on the adjustable sample fixture base 16.

At step 4, once the sample is positioned in the correct location for processing, the Capture switch 6 on the surface of the scanner is pressed. A digital optical image of the sample surface is captured by the high resolution camera and saved by the smart application into a file specific for the sample. Surface dimensional measurements and total sample volume are calculated from the optical image by the smart application and saved into the sample data file. If the sample is mounted or inaccessible for individual weight measurement, the volume calculation is correlated against a custom database to determine an accurate carat weight appropriate for the sample type. The carat weight information is saved into a data file specific to the sample.

At step 5, the Identify switch 4 on the surface of the scanner is pressed activating the coherent light source and the internal rotating optical mirror 24.

At step 6, the emitted radiation reflected back from the sample is collected by the high resolution camera and transmitted to the processor and a Raman spectral fingerprint is generated by the smart application. Erroneous spectral features are identified and removed from the sample spectrum by the smart application software. The resulting spectral fingerprint is saved by the smart application into a data file specific to the sample.

At step 7, the smart application compares the Raman spectral signature of the emitted radiation from the subject against one or more samples to determine if the spectral signature of the emitted radiation matches one of the one or more samples. This can be accomplished by, for example, correlating a Raman signature of the subject to spectra in a custom database and determining one or more best matches within a predetermined confidence level. If no matches are found within the predetermined confidence level a "No Match Found" response is generated. Sample spectra taken from multiple locations on the surface of an inhomogeneous subject can be added together to generate a composite spectrum by the smart application software. A sample spectrum can also be subtracted from that of another known substance to isolate unique spectral features for identification.

At step 8, the "Best Match" response, or a "No Match Found" response is forwarded to an operator and is also saved by the smart application in a data file specific to the sample.

At step 9, the sample is placed into the test fixture precision scale 15 for an accurate weight determination. This data is forwarded to the smart application where it is correlated against a custom database to determine an accurate carat weight appropriate for the sample type. The physical weight and carat weight information are saved into a data file specific to the sample.

At step 10, a test report containing all determinations, measurements and calculations is generated for the sample under test. The test report can be provided in hardcopy or softcopy form and can be transmitted remotely via communications paths or wirelessly.

Although various embodiments are specifically illustrated and described herein, it will be appreciated that modifications and variations of the invention are covered by the above teachings and are within the purview of the appended claims without departing from the spirit and intended scope of the invention. For example, certain applications of the Universal Tool for Automated Gam and Mineral Identification and Measurement herein are discussed, but the invention is not limited to these applications as other applications would be apparent from review of this application. Furthermore, these examples should not be interpreted to limit the modifications and variations of the invention covered by the claims but are merely illustrative of possible variations.

What is claimed is:

1. An apparatus for performing nondestructive materials analysis on a gem or mineral subject comprising:
   a white light source outputting white light;
   a coherent light source outputting coherent light;
   a high resolution camera;
   a processor coupled to the high resolution camera;
   said processor to output a first spectral fingerprint of the coherent light reflected from the subject;
   said processor to output a second spectral fingerprint of the white light reflected from the subject;
   a single optical path for transmitting both the coherent light reflected from subject and the white light reflected from the subject, wherein said single optical path includes:
     a fiber optic probe to pass the white light generated from the white light source to the subject and to collect any reflected light due to the white light from the subject, and to pass the coherent light generated from the coherent light source to the subject and to collect any reflected light due to the coherent light from the subject;
     a prism having a first side coated such that white light output from the white light source passes through the prism on the first side to a second side, said second side being coated so that the white light passing through the first side is reflected by the second side towards the fiber optic probe;
     said prism having said second side coated such that coherent light output from the coherent light source passes through the prism on the second side to the first side, said first side being coated so that the coherent light passing through the second side is reflected by the first side towards the fiber optic probe;
     said prism having a third side and a fourth side, both of which are uncoated so that any reflected light output from the fiber optic probe passes through the prism;
     a rotating minor that is rotatable into the optical path when coherent light is being directed towards the subject and is rotatable out of the optical path when white light is being directed towards the subject;
     a first mirror;
     a second mirror;
     an optical gradient separating light reflected by the subject into its spectral components;
     said rotating mirror directing light from the prism towards the first mirror, which directs light from the rotating minor towards the optical gradient;
     said optical gradient directing the spectral components of the light reflected by the subject to the second minor, which then directs the spectral components to the high resolution camera;
   a database to store a plurality of spectral fingerprints of a plurality of known samples and a plurality of physical parameters of known samples; and
   a processor coupled to the database, and the high resolution camera to compare the first spectral fingerprint and the second spectral fingerprint from the subject to the plurality of spectral fingerprints of the plurality of known samples in the database;
   a custom smart application executed by the processor to enable the processor to determine sample surface and volume measurements from image data captured by the optical imager, wherein said processor also determines one or more physical parameters of the sample from the sample surface and volume measurements and compares the one or more physical parameters to the plurality of physical parameters of known samples stored in the database;

a remotely or manually controlled translatable mounting platform that can be directed to reposition samples with a high degree of accuracy enabling precision analysis of multiple sample sites; and a housing to prevent ambient light from interfering with a Raman analysis of the sample.

2. The apparatus according to claim 1, further comprising:
one or more focused coherent light sources to illuminate the subject; and
one or more cameras to capture emitted radiation from the subject.

3. The apparatus according to claim 1, further comprising:
a white light source to illuminate the subject; and
one or more cameras to capture reflected light from the subject.

4. The apparatus according to claim 2, wherein the one or more focused coherent light sources comprise one or more lasers.

5. The apparatus according to claim 2, wherein the one or more cameras comprise one or more charge coupled devices.

6. An universal apparatus for performing portable on-site automatic nondestructive materials analysis and report generation on a gem or mineral subject comprising:
one or more focused coherent light sources to illuminate the subject;
one or more highly sensitive cameras to capture emitted radiation from the subject;
a white light source to illuminate the subject;
said one or more a highly sensitive cameras to capture reflected light from the subject;
a single optical path for the transmission and reception of the radiation for both the white light and focused coherent light including:
a fiber optic probe to pass the white light generated from the white light source to the subject and to collect any reflected light due to the white light from the subject, and to pass the coherent light generated from the coherent light source to the subject and to collect any reflected light due to the coherent light from the subject;
a prism having a first side coated such that white light output from the white light source passes through the prism on the first side to a second side, said second side being coated so that the white light passing through the first side is reflected by the second side towards the fiber optic probe;
said prism having said second side coated such that coherent light output from the coherent light source passes through the prism on the second side to the first side, said first side being coated so that the coherent light passing through the second side is reflected by the first side towards the fiber optic probe;
said prism having a third side and a fourth side, both of which are uncoated so that any reflected light output from the fiber optic probe passes through the prism;
a rotating minor that is rotatable into the optical path when coherent light is being directed towards the subject and is rotatable out of the optical path when white light is being directed towards the subject;
a first mirror;
a second mirror;
an optical gradient separating light reflected by the subject into its spectral components;

said rotating mirror directing light from the prism towards the first mirror, which directs light from the rotating minor towards the optical gradient;
said optical gradient directing the spectral components of the light reflected by the subject to the second minor, which then directs the spectral components to the high resolution camera;

a precision scale for the generation of subject weight;

an adjustable test sample fixture base to enable subject repositioning without the need to physically remove and remount the subject from the test holder;

removable specimen holders for the evaluation of both small and large test samples:
locking tweezers to securely capture smaller test samples in an orientation optimal for evaluation, and
a sample tray for ease of evaluating large or irregular shaped test samples;

a searchable database to store a plurality of spectral fingerprints of known samples and to store a plurality of standard gem and mineral physical weight to carat weight correlation factors;

a processor executing a smart application:
to compare a spectral signature in the emitted radiation from the subject to the plurality of spectral fingerprints of known samples in the database;
to save and store digital optical images and calculate physical measurements of the subject to include surface dimensions and total volume;
to store sample weight and calculate actual sample carat weight using the sample type identification and correlation factors in the searchable database;
to generate a unique software file for each sample and collocate all of the measured and calculated spectral, optical, and physical data;
to generate and transmit custom subject reporting; and
to enable the automated updating of the searchable databases locally or remotely; and a housing to prevent ambient light from interfering with the analysis of the sample.

7. The apparatus according to claim 6, wherein the processor includes a communication link via which the processor communicates with the scanner and test fixture.

8. The apparatus according to claim 6, wherein said processor generates a "positive/negative" or a "best match" response within a predetermined confidence level and forwards a result to an operator, wherein the response is saved to a data file generated to be unique for the subject under evaluation.

9. The apparatus according to claim 6, further comprising a memory, wherein said processor saves spectral, optical, and physical data from the subject in the memory and resets for a next subject for rapid evaluation of multiple samples.

10. The apparatus according to claim 6, further comprising a sample mounting fixture that is remotely or physically movable with high precision in an x-direction, a y-direction, and a z-direction.

11. The apparatus according to claim 10, wherein the sample mounting fixture enables examination of multiple locations on a surface or depth of the subject without physically repositioning the subject within the test fixture.

12. The apparatus according to claim 10, wherein the sample mounting fixture further comprises an adjustable mounting fixture base and x, y, and z positioning knobs attached to the adjustable mounting fixture base which permit the sample location to be tested to be moved by the operator automatically using the scanner or physically using x, y, and z positioning knobs.

13. The apparatus according to claim 1, further comprising a computer readable media having encoded thereon instructions that cause the processor smart application to automate capture and correlation of a Raman signature of the subject to spectra in the database and determine a best match or matches within a predetermined confidence level, wherein if no matches are found within the predetermined confidence level a "No Match Found" response will be generated and forwarded to the operator and saved into a data file unique to the sample under evaluation.

14. The apparatus according to claims 6, further comprising a computer readable media having stored thereon software to enable the processor smart application to filter out erroneous spectral features in a sample signature.

15. The apparatus according to claim 1, further comprising a computer readable media having stored thereon spectral correlation software to enable the processor smart application to provide on-site automated sample identification.

16. The apparatus according to claim 6, further comprising a computer readable media having stored thereon spectral correlation software to enable the processor smart application to provide on-site sample authenticity verification and proof of tampering or adulteration.

17. The apparatus scanner according to claim 6, further comprising a computer readable media having stored thereon spectral correlation software to enable the processor smart application to provide capability to automatically trace a material to its geological origin or manufacturer using a database of known Raman signatures.

18. The apparatus according to claim 6, further comprising a memory, wherein the processor can use stored optical image data to generate accurate physical measurements of a subject surface and calculate total volume to be saved in the memory in a data file unique for the subject under evaluation.

19. A method for performing nondestructive materials analysis on a gem or mineral subject comprising:
scanning the subject using a Raman scanner to obtain a first spectral fingerprint of coherent light reflected from the subject;
scanning the subject to obtain a second spectral fingerprint of white light reflected from the subject;
using a single optical path for transmission and reception of the white light and the coherent light reflected from the subject, wherein the single optical path includes:
wherein said single optical path includes:
a fiber optic probe to pass the white light generated from the white light source to the subject and to collect any reflected light due to the white light from the subject, and to pass the coherent light generated from the coherent light source to the subject and to collect any reflected light due to the coherent light from the subject;
a prism having a first side coated such that white light output from the white light source passes through the prism on the first side to a second side, said second side being coated so that the white light passing through the first side is reflected by the second side towards the fiber optic probe;
said prism having said second side coated such that coherent light output from the coherent light source passes through the prism on the second side to the first side, said first side being coated so that the coherent light passing through the second side is reflected by the first side towards the fiber optic probe;
said prism having a third side and a fourth side, both of which are uncoated so that any reflected light output from the fiber optic probe passes through the prism;
a rotating minor that is rotatable into the optical path when coherent light is being directed towards the subject and is rotatable out of the optical path when white light is being directed towards the subject;
a first mirror;
a second mirror;
an optical gradient separating light reflected by the subject into its spectral components;
said rotating mirror directing light from the prism towards the first mirror, which directs light from the rotating minor towards the optical gradient;
said optical gradient directing the spectral components of the light reflected by the subject to the second minor, which then directs the spectral components to the high resolution camera;
comparing the first spectral finger print against a plurality of spectral fingerprints of a plurality of known samples stored in a searchable database;
comparing the second spectral finger print against a plurality of spectral fingerprints of a plurality of known samples stored in the searchable database;
weighing the subject to determine a carat weight of the subject;
measuring the subject to determine a volume of the subject;
determining the density of the subject;
comparing the density of the subject against a density of a plurality of known samples stored in a database; and
enclosing the subject and the Raman scanner with a housing to prevent ambient light from interfering with the Raman analysis of the subject.

* * * * *